United States Patent
Tenarvitz et al.

(10) Patent No.: US 9,922,167 B2
(45) Date of Patent: Mar. 20, 2018

(54) CONTEXT-AWARE METHOD AND SYSTEM FOR FACILITATING THE DELIVERY OF HEALTHCARE TO PATIENTS WITHIN A CLINICAL ENVIRONMENT MONITORED BY REAL-TIME LOCATING APPARATUS

(75) Inventors: Henry J. Tenarvitz, Suttons Bay, MI (US); Hall T. Snowday, Traverse City, MI (US); Gary Gaisser, Kingsley, MI (US)

(73) Assignee: VERSUS TECHNOLOGY, INC., Traverse City, MI (US)

( * ) Notice: Subject to any disclaimer, the term of this patent is extended or adjusted under 35 U.S.C. 154(b) by 244 days.

(21) Appl. No.: 12/622,882

(22) Filed: Nov. 20, 2009

(65) Prior Publication Data
US 2011/0125524 A1    May 26, 2011

(51) Int. Cl.
*G06Q 50/00*    (2012.01)
*G06Q 10/00*    (2012.01)
(Continued)

(52) U.S. Cl.
CPC ............ *G06F 19/327* (2013.01); *G06Q 50/22* (2013.01); *G06Q 50/24* (2013.01)

(58) Field of Classification Search
CPC ..................................................... G06Q 50/00
See application file for complete search history.

(56) References Cited

U.S. PATENT DOCUMENTS 4,868,859 A    9/1989 Sheffer
4,906,853 A    3/1990 Linwood et al.
(Continued)

OTHER PUBLICATIONS

ProQuest Result, "Tools of the Trade" Buildings. Feb. 2006 vol. 100 Issue 2, pp. 60-74 (Year: 2006).*

(Continued)

*Primary Examiner* — Neal Sereboff
(74) *Attorney, Agent, or Firm* — Frost Brown Todd LLC

(57) ABSTRACT

A context-aware method and system for facilitating the delivery of healthcare to patients within a clinical environment monitored by real-time locating apparatus including auto-ID patient tags where patients having tags are located within the environment in real time by the apparatus are provided. The system includes a plurality of self-service units where one or more of the units is configured to store a plurality of auto-ID patient tags and where the one or more of the units includes a dispensing mechanism to dispense stored tags. The system further includes a control computer subsystem coupled to the at least one of the units and including at least one user interface. The subsystem still further includes a processor operable to execute software instructions and a memory operable to store software instructions accessible by the processor. The subsystem still further includes a set of software instructions stored in the memory to at least partially perform the steps of: identifying an incoming patient; assigning a stored auto-ID patient tag to the identified patient to obtain a tag assignment; transmitting a signal over a communication channel to an electronic medical record subsystem to link the tag assignment to a medical record of the patient whereby the patient becomes a linked patient; and controlling the dispensing mechanism to dispense a stored tag to the linked patient.

20 Claims, 8 Drawing Sheets

(51) Int. Cl.

| | | |
|---|---|---|
| *G06Q 20/00* | (2012.01) | |
| *G08B 1/08* | (2006.01) | |
| *G06F 17/00* | (2006.01) | |
| *G06F 19/00* | (2018.01) | |
| *G06Q 50/22* | (2018.01) | |
| *G06Q 50/24* | (2012.01) | |

(56) References Cited

U.S. PATENT DOCUMENTS

| | | | |
|---|---|---|---|
| 5,017,794 A | 5/1991 | Linwood et al. | |
| 5,027,314 A | 6/1991 | Linwood et al. | |
| 5,027,383 A | 6/1991 | Sheffer | |
| 5,119,104 A | 6/1992 | Heller | |
| 5,131,019 A | 7/1992 | Sheffer et al. | |
| 5,276,496 A | 1/1994 | Heller et al. | |
| 5,355,222 A | 10/1994 | Heller et al. | |
| 5,387,993 A | 2/1995 | Heller et al. | |
| 5,548,637 A | 8/1996 | Heller et al. | |
| 5,572,195 A | 11/1996 | Heller et al. | |
| 6,104,295 A | 8/2000 | Gaisser et al. | |
| 6,154,135 A | 11/2000 | Kane et al. | |
| 6,154,139 A * | 11/2000 | Heller | G08B 3/1083 340/572.1 |
| 6,308,886 B1 * | 10/2001 | Benson | G06K 17/00 235/375 |
| 6,462,656 B2 | 10/2002 | Ulrich et al. | |
| 6,707,381 B1 | 3/2004 | Maloney | |
| 6,838,992 B2 * | 1/2005 | Tenarvitz | G01S 5/16 340/572.1 |
| 7,113,088 B2 | 9/2006 | Frick et al. | |
| 7,118,027 B2 * | 10/2006 | Sussman | G06Q 20/341 235/375 |
| 7,205,889 B2 | 4/2007 | Howe, Jr. et al. | |
| 7,317,393 B2 | 1/2008 | Maloney | |
| 7,348,884 B2 | 3/2008 | Higham | |
| 7,490,054 B2 | 2/2009 | Reade et al. | |
| 7,541,926 B2 | 6/2009 | Dugan et al. | |
| 2001/0041994 A1 * | 11/2001 | Kim | G06Q 10/02 705/5 |
| 2003/0050821 A1 | 3/2003 | Brandt et al. | |
| 2003/0052787 A1 * | 3/2003 | Zerhusen | A47B 23/046 340/573.1 |
| 2004/0138924 A1 | 7/2004 | Pristine | |
| 2004/0186744 A1 | 9/2004 | Lux | |
| 2004/0193449 A1 * | 9/2004 | Wildman | G06F 19/327 705/2 |
| 2005/0110640 A1 | 5/2005 | Chung | |
| 2005/0261942 A1 | 11/2005 | Wheeler | |
| 2006/0080819 A1 * | 4/2006 | McAllister | G06K 17/00 29/403.3 |
| 2006/0111941 A1 * | 5/2006 | Blom | G06Q 10/06 705/2 |
| 2006/0161435 A1 * | 7/2006 | Atef | G06F 21/31 704/246 |
| 2006/0218626 A1 | 9/2006 | Goehler | |
| 2006/0277071 A1 | 12/2006 | Shufeldt | |
| 2007/0136154 A1 | 6/2007 | Chung | |
| 2007/0226010 A1 | 9/2007 | Larsen | |
| 2007/0288263 A1 | 12/2007 | Rodgers | |
| 2008/0040421 A1 | 2/2008 | VanKoevering | |
| 2008/0118045 A1 * | 5/2008 | Polozola | H04M 11/007 379/167.14 |
| 2008/0121699 A1 * | 5/2008 | Thorsen | G07C 9/00007 235/381 |
| 2008/0211671 A1 | 9/2008 | Daily | |
| 2008/0249883 A1 | 10/2008 | Daily | |
| 2008/0252414 A1 | 10/2008 | Crigger et al. | |
| 2008/0277466 A1 * | 11/2008 | Dohm | G06Q 10/06 235/382 |
| 2008/0306759 A1 | 12/2008 | Ilkin et al. | |
| 2009/0043253 A1 * | 2/2009 | Podaima | G06Q 10/10 604/67 |
| 2009/0070142 A1 | 3/2009 | Morita et al. | |
| 2009/0076875 A1 * | 3/2009 | Lert, Jr. | G06Q 30/016 705/14.3 |
| 2009/0111562 A1 * | 4/2009 | Chudd | G07D 7/0006 463/20 |
| 2009/0206992 A1 | 8/2009 | Giobbi | |
| 2009/0281825 A1 | 11/2009 | Larsen | |
| 2009/0289776 A1 * | 11/2009 | Moore | G06K 7/0008 340/10.41 |
| 2011/0191124 A1 | 8/2011 | Sung et al. | |

OTHER PUBLICATIONS

International Search Report and Written Opinion; International Application No. PCT/US2010/35088; dated Jul. 9, 2010.
Notice of Acceptance; corresponding Australian Application No. 2010322438; dated Nov. 5, 2013.
Patent Examination Report No. 1; Australian application No. 2010322438; dated Jul. 18, 2013.
International Preliminary Report on Patentability, Written Opinion of the International Searching Authority; International Application No. PCT/US2010/035088; dated May 22, 2012.
Office Action No. 10136 issued from the Mexican Institute of Industrial Property; Mexican patent application No. Mx/a/2012/005803.
Extended European Search Report; corresponding European patent application No. 10831925.2; dated Nov. 19, 2013.
Notice of Allowance, communication No. 4683; corresponding Mexican patent application No. Mx/a/2012/005802; dated Jan. 22, 2015.
Canadian Office Action dated Oct. 24, 2016 for Application No. CA 2,780,914, 3 pgs.
First Office Action dated Jan. 5, 2016, Canadian Patent Application No. 2,780,914, 3 pages.

* cited by examiner

Dr. Smith, please sanitize your hands before visiting patient Doe

Alert

Unit 5 East
Overall compliance
Current Shift

CONTEXT-AWARE METHOD AND SYSTEM FOR FACILITATING THE DELIVERY OF HEALTHCARE TO PATIENTS WITHIN A CLINICAL ENVIRONMENT MONITORED BY REAL-TIME LOCATING APPARATUS

CROSS-REFERENCE TO RELATED APPLICATION

This application is related to commonly owned U.S. application Ser. No. 12/622,959, filed Nov. 20, 2009 (the same day as this application) and entitled "Real-Time Method And System For Controlling Healthcare Delivery Processes Within A Clinical Environment."

BACKGROUND OF THE INVENTION

1. Field of the Invention

This invention relates to context-aware methods and systems for facilitating the delivery of healthcare to patients within a clinical environment monitored by real-time locating apparatus. At least one embodiment of the invention relates to methods and systems for monitoring and improving healthcare delivery processes within a clinical environment monitored by a real-time locating system (RTLS).

2. Background Art

As disclosed in U.S. Pat. Nos. 6,154,135 and 6,838,992 auto-ID tags or badges are assigned to patients upon patient check-in or registration in a healthcare facility. Such tags emit radio-frequency (RF) and other signals such as infrared (IR) signals. The signals are used to establish the real-time location of the patients in a real-time locating system.

The ongoing assignment of such tags or badges to patients and the deletion of former badge assignments from the system requires frequent maintenance. This assignment and deletion has been done in the past with a computer system.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations.

Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

Patients may access information systems for scheduling, diagnosis and/or treatment information, check-in or admission, and/or other tasks. One or more of these systems comprise a healthcare information system, for example.

In typical healthcare settings, the patient registration process is a lengthy and repetitive procedure that patients must endure at nearly every encounter with a healthcare professional. Each new doctor, office, department, or even visit often requires a new set of forms to be completed. Moreover, paper-based forms are still widely used to document a patient's demographic information, medical history, current medications, allergies, and other information. These paper-based forms are often added to the patient's folder associated with the particular doctor, department, or office being visited. In many settings, the information provided by the patient is transcribed into an electronic healthcare information system. Of course, the transcription process is prone to error in data entry and necessarily results in the patient losing control of his or her data.

In more advanced healthcare enterprises, patients have the ability to input their relevant information directly into an electronic system, thus bypassing the transcription process. For example, kiosk systems enable patients to enter their information at a kiosk that aggregates and transmits the information to the healthcare information system. A kiosk is a small self-standing physical structure (often including a computer and a display screen) that displays information for people walking by. More sophisticated kiosks let users interact and include touch screens, keyboards, sound, and motion video. Examples of kiosk systems are disclosed in the following U.S. patent documents: 2004/0138924; 2004/0186744; 2005/0261942; 2006/0277071; 2007/0226010; and 2008/0040421.

U.S. Patent document 2009/0070142 discloses a method and system for providing patient registration information. The method includes requesting patient data, supplying the patient data using a mobile electronic device, storing the patient data to a memory associated with the mobile electronic device, and communicating the patient data to a remote data server.

The following U.S. patent documents disclose methods, systems and/or kiosks for objects and/or information and which are related to at least one embodiment of the present invention: 2007/0136154; 2008/0211671; 2008/0249883; 2008/0252414; U.S. Pat. Nos. 6,707,381; 7,113,088; 7,205,889; 7,317,393; 7,348,884; and 7,490,054.

The following U.S. patents are also related to the present invention: U.S. Pat. Nos. 4,868,859; 4,906,853; 5,017,794; 5,027,314; 5,027,383; 5,119,104; 5,131,019; 5,276,496; 5,355,222; 5,387,993; 5,548,637; 5,572,195; 6,104,295; 6,154,139; 6,462,656; and 6,838,992.

Despite the above prior art methods and systems, advances in medical science are causing processes for delivery of healthcare to continually grow more complex and costly. The effects caused by the increased complexity include greater opportunity for the introduction of human error and omission as well as higher staff related expenses incurred to deliver high quality care within the advanced technological healthcare environment.

SUMMARY OF THE INVENTION

One or more steps of at least one embodiment of the invention may be implemented alone or in combination in hardware, firmware, and/or as a set of instructions in software. Certain embodiments may be provided as a set of instructions residing on a computer-readable medium, such as a memory, CD, DVD, or hard disk, for execution on a general purpose computer or other processing device, such as, for example, a PC workstation.

An object of the present invention is to provide a context-aware method and system for facilitating the delivery of healthcare to patients within a clinical environment monitored by real-time locating apparatus.

Another object of at least one embodiment of the present invention is to provide a system which employs SSTs or non-attached kiosks to streamline and reduce the introduction of error into the patient flow process by defining and monitoring common healthcare delivery processes involving mobile, tag-wearing subjects that increase the efficiency of delivery and the safety of each process; are simple and inexpensive to operate and maintain; require no special training for clinical staff; and that leverage common, pre-existing communication infrastructure, when possible.

Yet another object of at least one embodiment of the present invention is to increase the efficiency and safety of common healthcare delivery processes in a clinical setting by providing strategically placed, context-aware SSTs or non-attached kiosks to admit, direct and discharge patients. The context awareness is generated through a process of collecting RTLS data as well as other event data captured from a clinical data source (CDS), including any systems or databases accessible by the RTLS such as a clinical information basing system such as SQL, operating concurrently with the clinical setting. The RTLS evaluates the data elements in any given predefined rule and responds with the corrective actions when process performance degrades below acceptable limits. All data collected is provided to the SST, as needed.

In carrying out the above object and other objects of the present invention, a context-aware system for facilitating the delivery of healthcare to patients within a clinical environment monitored by real-time locating apparatus including auto-ID patient tags where patients having tags are located within the environment in real time by the apparatus is provided. The system includes a plurality of self-service units where one or more of the units is configured to store a plurality of auto-ID patient tags and where the one or more of the units includes a dispensing mechanism to dispense stored tags. The system further includes a control computer subsystem coupled to the at least one of the units and including at least one user interface. The subsystem also includes a processor operable to execute software instructions and a memory operable to store software instructions accessible by the processor. The subsystem further includes a set of software instructions stored in the memory to at least partially perform the steps of: identifying an incoming patient; assigning a stored auto-ID patient tag to the identified patient to obtain a tag assignment; transmitting a signal over a communication channel to an electronic medical record subsystem to link the tag assignment to a medical record of the patient whereby the patient becomes a linked patient; and controlling the dispensing mechanism to dispense a stored tag to the linked patient.

The system may include means for authenticating a user of the control computer subsystem as an authorized patient based, at least in part, on an authenticator. The authenticator may include at least one of a password, a pass phrase, a personal identification number, a security token, a security card, and a biometric identifier.

The biometric identifier may include at least one of a fingerprint, a retinal pattern, an infrared vein pattern, a signature, a voice, a face, a bio-electric signal, and a DNA sequence.

Each dispensed tag may be sanitized.

The set of software instructions may at least partially perform the step of providing notification of arrival of the linked patient.

The step of identifying may include the step of receiving registration data at the at least one user interface where the registration data includes at least one of a medication history, an allergy, a medical problem, a family medical history, an insurance provider, an employer, a social security number, contact information, and demographic information.

The set of software instructions may at least partially perform the step of directing the linked patient where to proceed to begin a healthcare delivery process within the environment at the at least one user interface.

At least one of the units may include a receiving mechanism to receive previously dispensed tags and where the set of software instructions at least partially performs the step of transmitting a signal over the communication channel to the electronic medical record subsystem to delete the tag assignment from the medical record whereby the linked patient becomes unlinked.

The system may include means for sanitizing the received tags.

The set of software instructions may at least partially perform the steps of receiving discharge instructions over the communications channel from the electronic medical record subsystem and communicating the discharge instructions to the unlinked patient at the at least one user interface.

The set of software instructions may at least partially perform the step of receiving verifying data that the discharge instructions were received by the unlinked patient at the at least one user interface.

The set of software instructions may at least partially perform the steps of receiving education material specific to a diagnosis of the unlinked patient over the communication channel from the electronic medical record subsystem and communicating the education material to the unlinked patient at the at least one user interface.

The set of software instructions may at least partially perform the step of collecting payment from the unlinked patient.

The set of software instructions may at least partially perform the step of validating the payment.

The set of software instructions may at least partially perform the steps of communicating a satisfaction survey to the unlinked patient at the at least one user interface and receiving survey data from the unlinked patient at the at least one user interface.

The system may further include identifying a linked patient within a region about the at least one user interface where the set of software instructions at least partially performs at least one of the steps of: communicating context-tailored information regarding progression of a care delivery process of the linked patient at the at least one user interface; communicating context-tailored education content to the linked patient at the at least one user interface; determining whether content is communicated for a predetermined period of time to the linked patient at the at least one user interface; and issuing CE credit to the linked patient.

The at least one user interface may include at least one of a video camera, a display, a key pad or board, a microphone, a touch screen, and a printer.

Further in carrying out the above object and other objects of the present invention, a context-aware method for facilitating the delivery of healthcare to patients within a clinical environment monitored by real-time locating apparatus including auto-ID patient tags is provided. The method includes storing a plurality of auto-ID patient tags, identifying an incoming patient, and assigning a stored auto-ID patient tag to the identified patient to obtain a tag assignment. The method also includes transmitting a signal over a communication channel to an electronic medical record subsystem to link the tag assignment in a medical record of the patient whereby the patient becomes a linked patient. The method further includes controlling the dispensing of the stored auto-ID patient tag to the linked patient.

The method may further include authenticating the incoming patient as an authorized patient based, at least in part, on an authenticator, where the authenticator includes at least one of a password, a pass phrase, a personal identification number, a security token, a security card, and a biometric identifier.

The method may further include receiving of the previously dispensed tag from the linked patient and transmitting a signal over the communication channel to the electronic medical record subsystem to delete the tag assignment from the medical record wherein the linked patient becomes unlinked.

Still further in carrying out the above object and other objects of the present invention, a context-aware system for facilitating the delivery of healthcare to patients within a clinical environment monitored by real-time locating apparatus including auto-ID patient tags wherein patients having tags are located within the environment in real time by the apparatus is provided. The system includes a plurality of self-service units where one or more of the units is configured to store a plurality of auto-ID patient tags. Each of the tags is capable of transmitting a wireless signal including ID information upon actuation. The one or more of the units includes a dispensing mechanism to dispense stored tags and to actuate tags during dispensing of the tags so that each of the dispensed tags transmit a wireless signal. The system further includes a control computer subsystem coupled to the dispensing mechanism and including at least one user interface and a processor operable to execute software instructions. The subsystem further includes a memory operable to store software instructions accessible by the processor. The subsystem still further includes a set of software instructions stored in the memory to at least partially perform the steps of: identifying an incoming patient; assigning a stored auto-ID patient tag to the identified patient to obtain a tag assignment; transmitting a signal over a communication channel to an electronic medical record subsystem to link the tag assignment to a medical record of the patient whereby the patient becomes a linked patient; and controlling the dispensing mechanism to dispense a stored tag to the linked patient. The at least one of the units includes a first receiver coupled to the subsystem to receive the wireless signal including its associated ID information and provide the ID information to the subsystem.

At least one of the units may include a second receiver coupled to the subsystem and a receiving mechanism to receive previously dispensed tags and to actuate tags during receiving of the tags. The second receiver receives the wireless signals from the actuated tag during receiving of the tag and provides the ID information to the subsystem. The set of software instructions at least partially performs the step of transmitting a signal over the communication channel to the electronic medical record subsystem to delete the tag assignment from the medical record whereby the linked patient becomes unlinked.

The above object and other objects, features, and advantages of the present invention are readily apparent from the following detailed description of the best mode for carrying out the invention when taken in connection with the accompanying drawings.

DETAILED DESCRIPTION OF THE PREFERRED EMBODIMENT(S)

Figure 1:
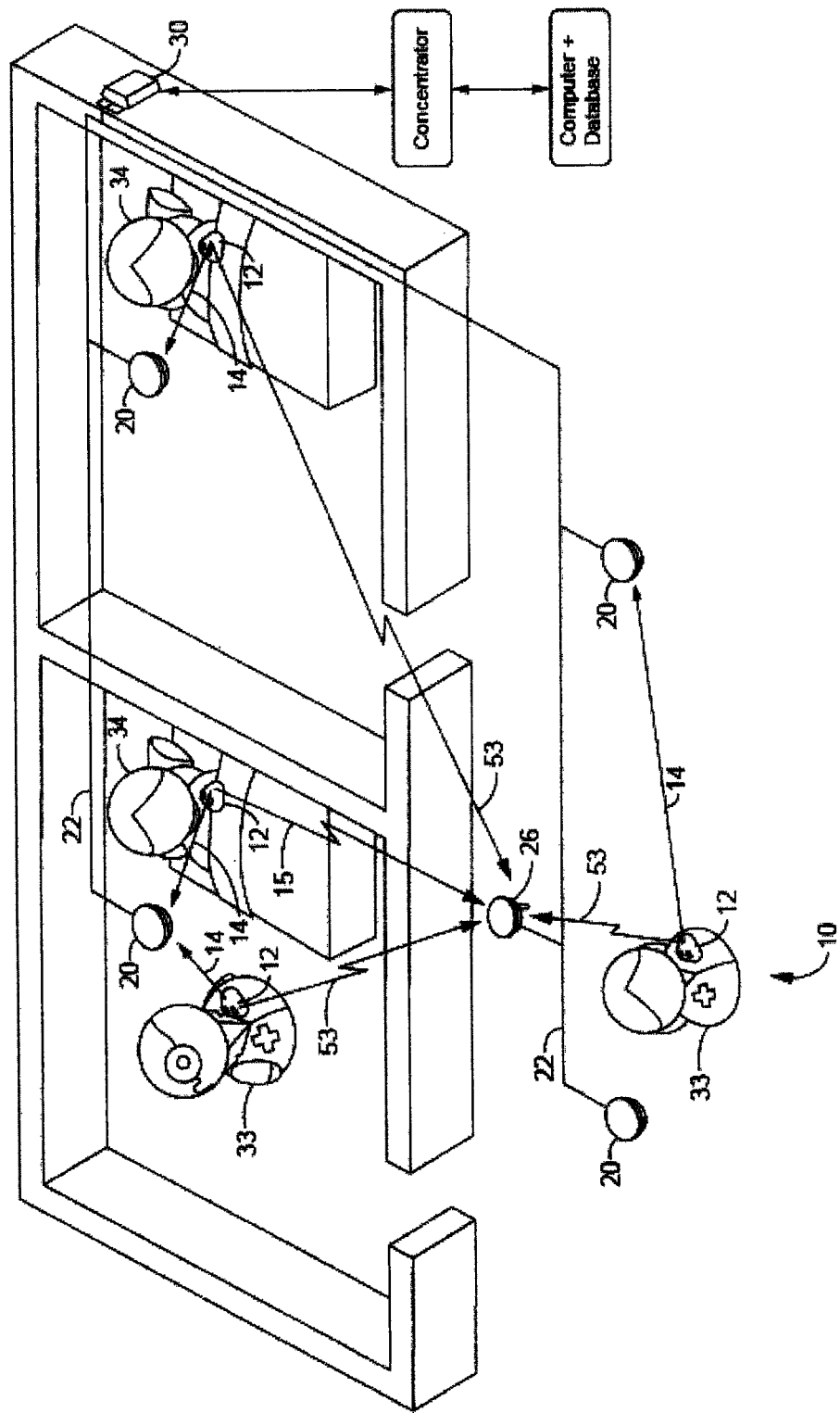
FIG. 1 is a schematic overview diagram illustrating a prior art method and apparatus for locating subjects within a clinical environment.

In general and in at least one embodiment of the present invention, methods and systems are provided to expedite patient flow through the use of non-attended kiosks or self-service terminals (SST) to:

1. Identify the incoming patient, issue a sanitized RTLS locating tag to that patient, establish a link between the unique ID of the RTLS tag and the patient's electronic medical record (EMR), provide notification of the patient's arrival and direct the patient to the beginning of their care delivery process;
2. Automatically identify linked patients that approach a kiosk or SST and provide them with information regarding the progression of their care delivery process; and
3. Automatically initiate the discharge process when the patient approaches designated discharge areas including issuing discharge instructions, collecting verifying data that discharge instructions were received, collecting payment and then collecting and sanitizing the patient's RTLS tag.

By using a SST or kiosk that has context awareness provided by the RTLS and access to patient EMR data, information can be communicated to and from the patient more quickly and with greater accuracy, making the care delivery process safer and more efficient.

The method and system of at least one embodiment of the invention aims to reduce healthcare delivery costs through a reduction in the amount of time skilled, paid staff members spend on processes that can be automated at the SST. Additionally, the potential for human error introduced during process delivery is mitigated.

Referring now to the drawing figures, an RTLS constructed in accordance with at least one embodiment of the invention comprises a number of concurrent processes. These include a tracking process 35 to collect tag 12 information in real time, a messaging process 37 to collect or issue non-tag data messages such as those from a CDS 39 pertinent to each tag 12, an evaluation process 38 to continually evaluate each rule respective to the current values stored or pointed to in the tag database 36 and execute actions if indicated. Actions 48 may be issued to the SST 49 from the evaluation process 38 and subject data collected from the SST 49 may result in a new action being issued by the evaluation process 38. Exchange of data from process to process is typically accomplished via a Local Area Network (LAN) 50 that may be connected to the Enterprise Network (Intranet) 51.

Figure 9:
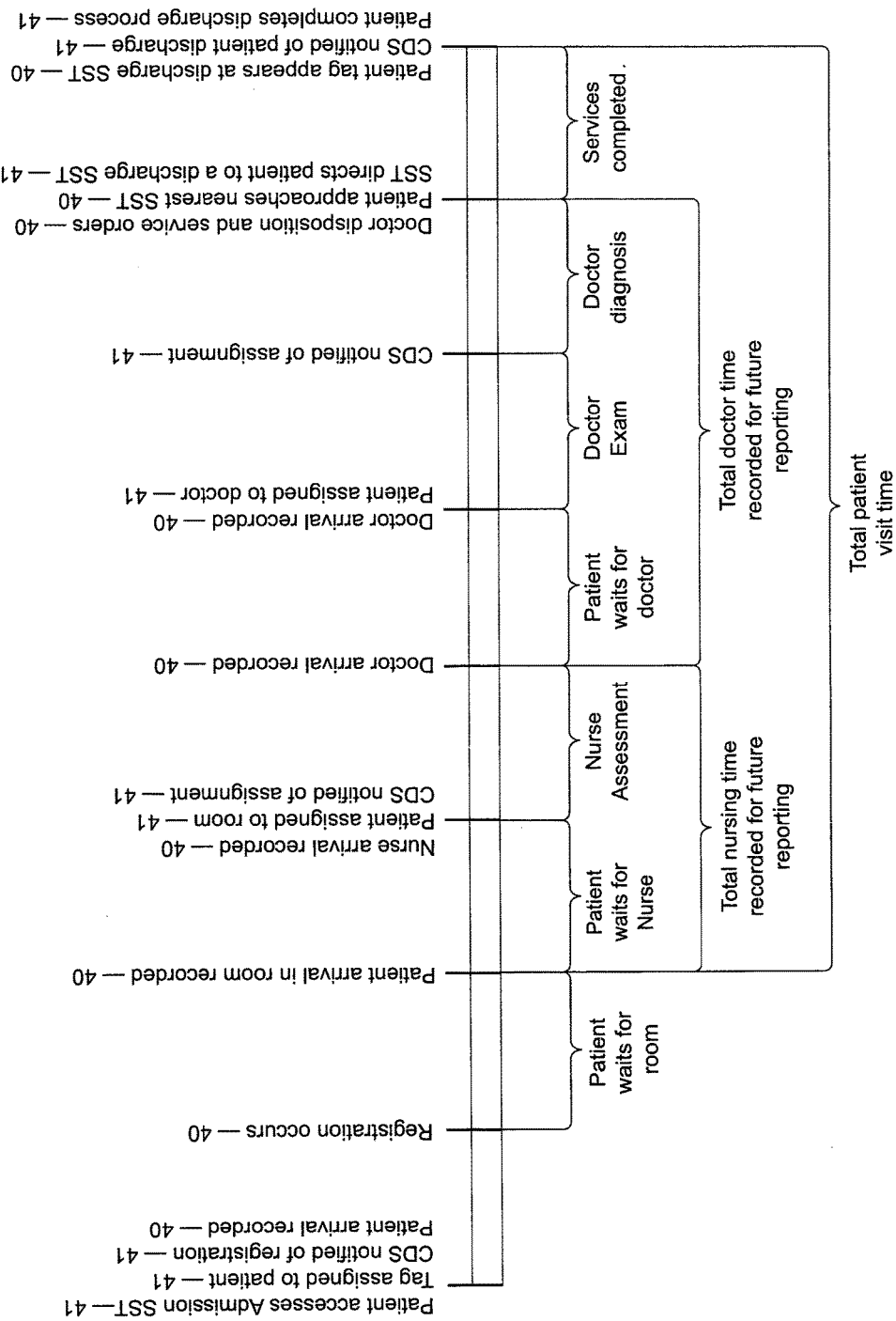
FIG. 9 is a time line for a patient and caregivers in a clinical environment illustrating the delivery of healthcare facilitated by at least one embodiment of the method and system of the present invention.

The tag database 36 stores tracking process 35, tag 12, specific event data 40 or non-tracking process subject data 41 (i.e., FIG. 9). Event data 40 includes the tag's location and switch state history. Subject data 41 includes data or pointers to data (information needed to retrieve the data from another source) such as name, medical record number or other data pertinent to each tag's 12 subject.

Figure 2:
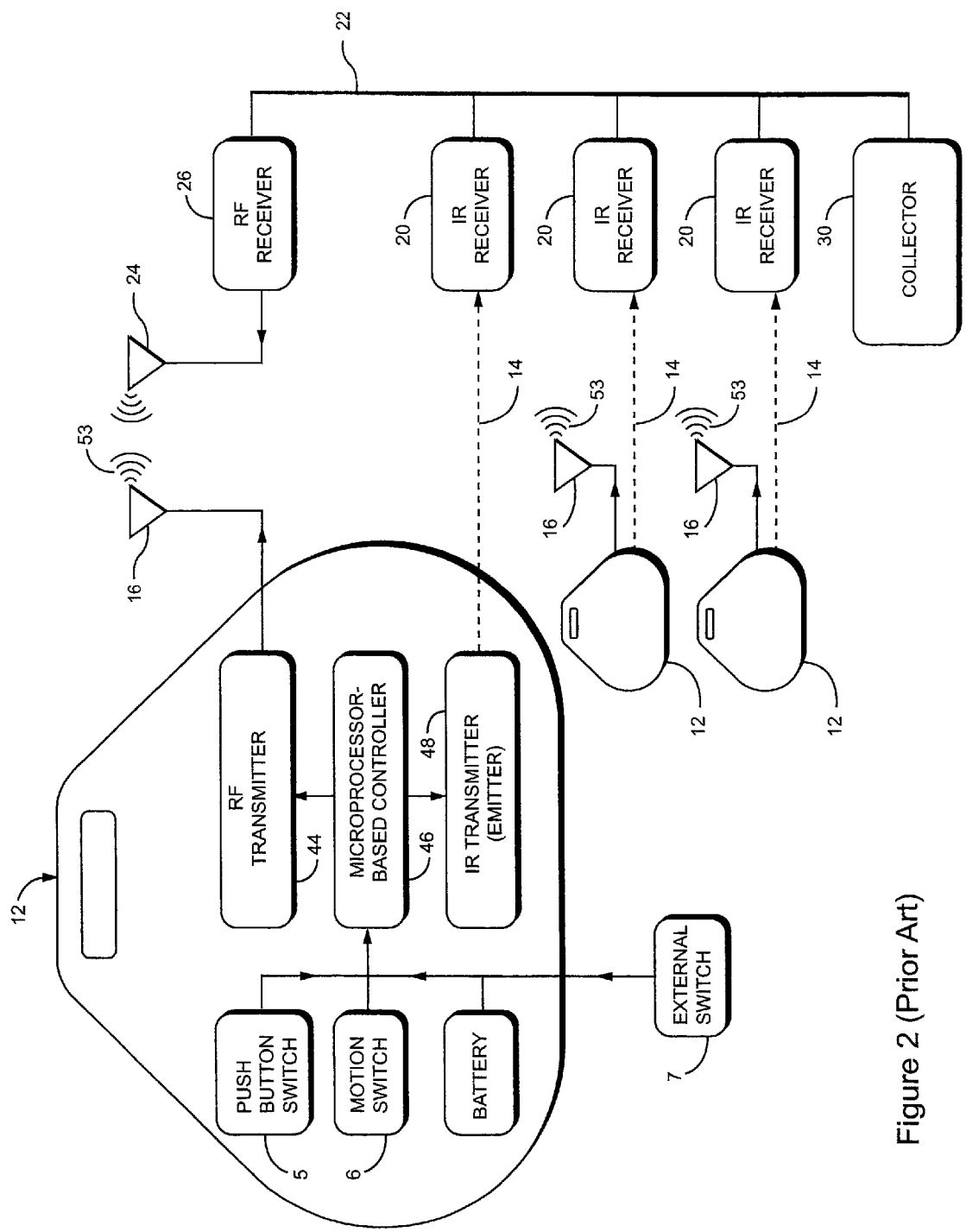
FIG. 2 is a schematic block diagram specifically illustrating a prior art auto-ID tag useful with the method and apparatus of FIG. 1 for locating subjects.

Referring specifically now to FIGS. 1 and 2, there is illustrated a real-time tracking system, generally indicated at 10, which may also be used to capture location change and alert events of each tag 12 wearing subject. Generally, the system 10 is comprised of tags 12 (worn by subjects or attached to objects) which emit infrared signals 14 which are captured by infrared receivers 20 common to the tracking system.

Figure 3:
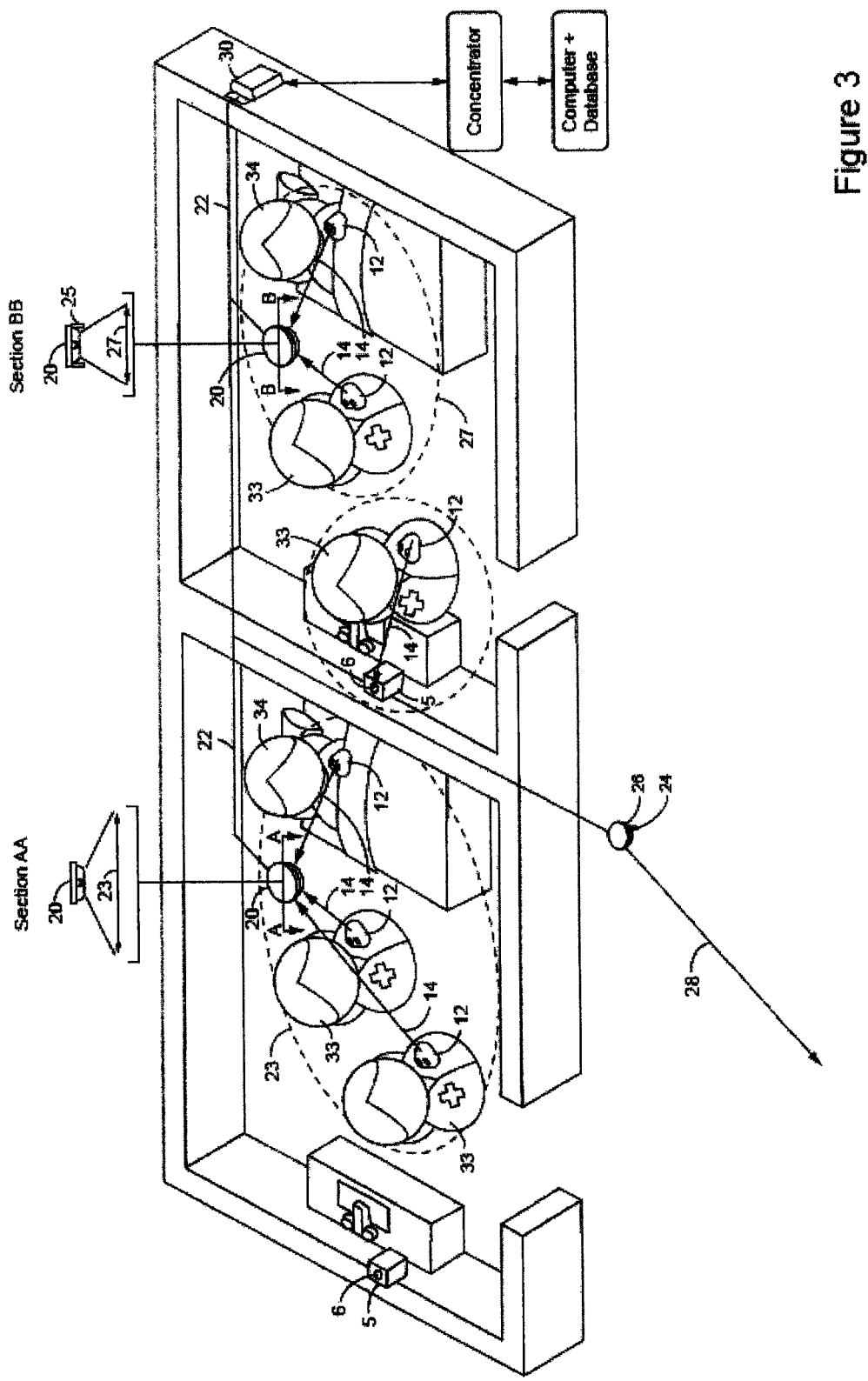
FIG. 3 is a diagram similar to the diagram of FIG. 1 but illustrating a pair of different IR receivers in section.

Typically, the maximum effective line-of-sight range of such infrared signals 14 is about a twenty meter diameter 23 (i.e., section A-A in FIG. 3). To achieve a more precise location within the system 10, the infrared receiver 20 may have its field of view reduced to as little as a one meter diameter 27 by introducing a restrictor 25 in the IR sensor 20 (i.e., section B-B in FIG. 3). The tags 12 may also transmit radio frequency (i.e., RF) signals 15 which are received by an RF receiver 26. The radio frequency signal 15 emitted by the antennas 16 are received by an antenna 24 of a radio frequency receiver 26 having a range of approximately forty meters 28 in all directions. Typically, information is collected using in-ceiling and/or in-wall sensors connected by a serial network 22 that terminates at the microprocessor-based collector 30.

The IR receiver 20 is stationary and its location is known. Tags 12 are worn by mobile subjects and transmit unique IDs 14 which allow the tracking system 10 to associate unique subject identifiers 41 (such as name, medical record number, tag type) to each individual tag 12. With this association, when IR signals 14 are received by an IR receiver 20 the tracking system 10 identifies the tag(s) 12 (and hence the subject or subjects) as being in the location associated with the IR receiver 20. The tracking system 10 aggregates the unique IDs received from the tags 12 enabling the system 10 to identify when one or more unique IDs are present at a particular location (represented by an IR sensor 20).

The tags 12 worn by mobile subjects may also incorporate one or more switches that when activated add an identifier to the signal 14 transmitted by the tag 12. Typical switch type include manual switches such as an externally accessible push button switch 5 on the tag 12, a motion switch 6 activated automatically by the tags 12 subject's motion or an external switch 7. When activated a switch may cause the tag 12 to transmit the modified signal immediately or it may transmit the modified signal during the next periodic transmission depending on the immediacy associated with that switch's function.

The messaging process has two functions. First, it monitors CDS 39 messages 46 typically via direct proprietary interface or standardized interface such as HL7, collects data 41 (FIG. 9) pertinent to each tag's 12 subject, then stores the data or points to the data 41 associated with that tag 12 in the tag database 36 for subsequent evaluation by the evaluation process 38. Second, it monitors requests for action 48 from the evaluation process 38 and communicates messages 46 to the device 49 or a CDS 39 pertinent to the evaluation of any given rule 43.

Figures 5, 6:
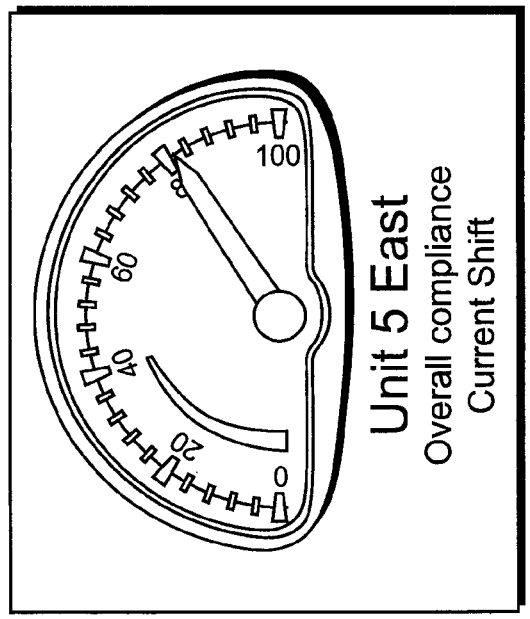
FIG. 5 is a view of a possible text alert that can be generated and displayed using at least one embodiment of the present invention.
FIG. 6 is a view of a dashboard type graphical indicator that can be generated and displayed using at least one embodiment of the present invention.

The evaluation process 38 continually evaluates each rule 48 in the rule set 42 using the most recent event data values stored. When the evaluation of a rule 43 indicates the need for an action 48 the evaluation process 38 interprets and executes the specific action 48 indicated by the rule 43 being evaluated. Specific actions 48 typically executed include:
1. Directing the messaging process 37 to communicate a specific message 46;
2. Directing a SST 49 to communicate audio or visual information. An example of this is shown in FIGS. 5 and 6; and
3. Activation of a remote relay(s) action 48 to manipulate a physical device such as a light or alarm.

Rule sets 42 are comprised of rules 43 that are structured as conditional statements typically taking the "IF THEN ELSE" or "CASE" ("SWITCH") forms. Examples of rules 43 are:

```
IF (event data 40 and/or subject data 41) TRUE
THEN (take action 48)
ELSE (take alternate action 48 or take no action)
CASE (RESULT = evaluated event data 40 and/or subject data 41)
VALUE 1 (take action 48)
VALUE 2 (take alternate action 48)
. . .
VALUE RESULT N (take alternate action 48)
```

Rules 43 are structured in such a way as to compare the progress of a patient, as represented by the current values stored in event data 40 and subject data 41 to value ranges that are known to represent optimized clinical process performance. Three very simplified examples are shown below:

```
IF      Tag 12 location = Radiology Information SST 49
THEN    Action 48 display Radiology Information SST 49
        Tag 12 subject information "Select from the following"
        "Display information regarding progress in my healthcare
        process"
        "Display information regarding the next phases in my healthcare
        process"
        "Display patient satisfaction survey options"
IF      Tag 12 location = Radiology Information SST 49 AND
        Tag 12 next phase = Phlebotomy Lab Informational SST 49
THEN    Action 48 Display "Radiology Information SST"
        Tag 12 subject information "Proceed to"
        Directions to location of Phlebotomy Lab Informational SST 49
IF      No tag 12 is present at Location Radiology Information SST 49
THEN    Action 48 Display "Radiology Information SST" HIPAA
        compliance clear screen
```

Figure 4:
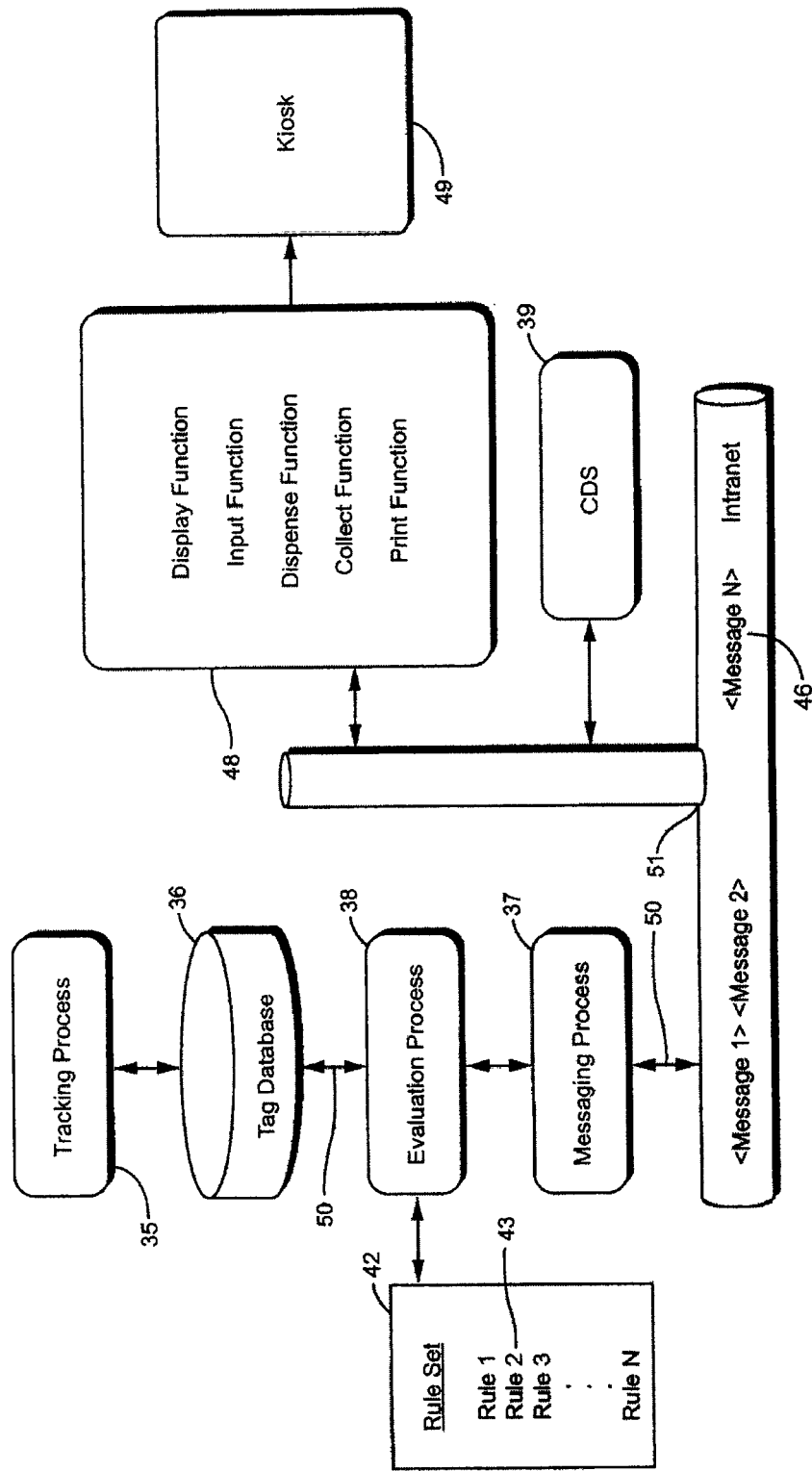
FIG. 4 is a schematic diagram of a system constructed in accordance with at least one embodiment of the present invention including a kiosk or SST and a control computer subsystem.

Referring now to FIG. 4, the admission SST 68 guides the patient through the registration process and provides guidance as to how to begin their healthcare delivery process. When the SST 49 is engaged by a person it will instruct the individual to present two forms of identification. The patient may use the keyboard of a user interface to enter their subject data 41:
1. Name
2. Birth date
3. Social security number
4. Health system ID number.

If available, the patient may also utilize the biometric fingerprint or iris scan identifying device. When any combination of two identification forms presented match those stored in the applicable CDS 39, the SST 49 will request the patient EMR subject identifier 41 from the appropriate CDS 39 and begin the registration process. Upon receiving basic identification, the SST 49 will ascertain the patient's unique EMR identifier necessary for retrieving additional information from any particular CDS 39. If the healthcare to be delivered requires a prearranged appointment, the SST 49 will validate that the scheduling is correct before admission continues. The dispenser unit 68 integrated into the SST 49 issues a reusable RTLS tag 12 to the patient.

Figure 7:
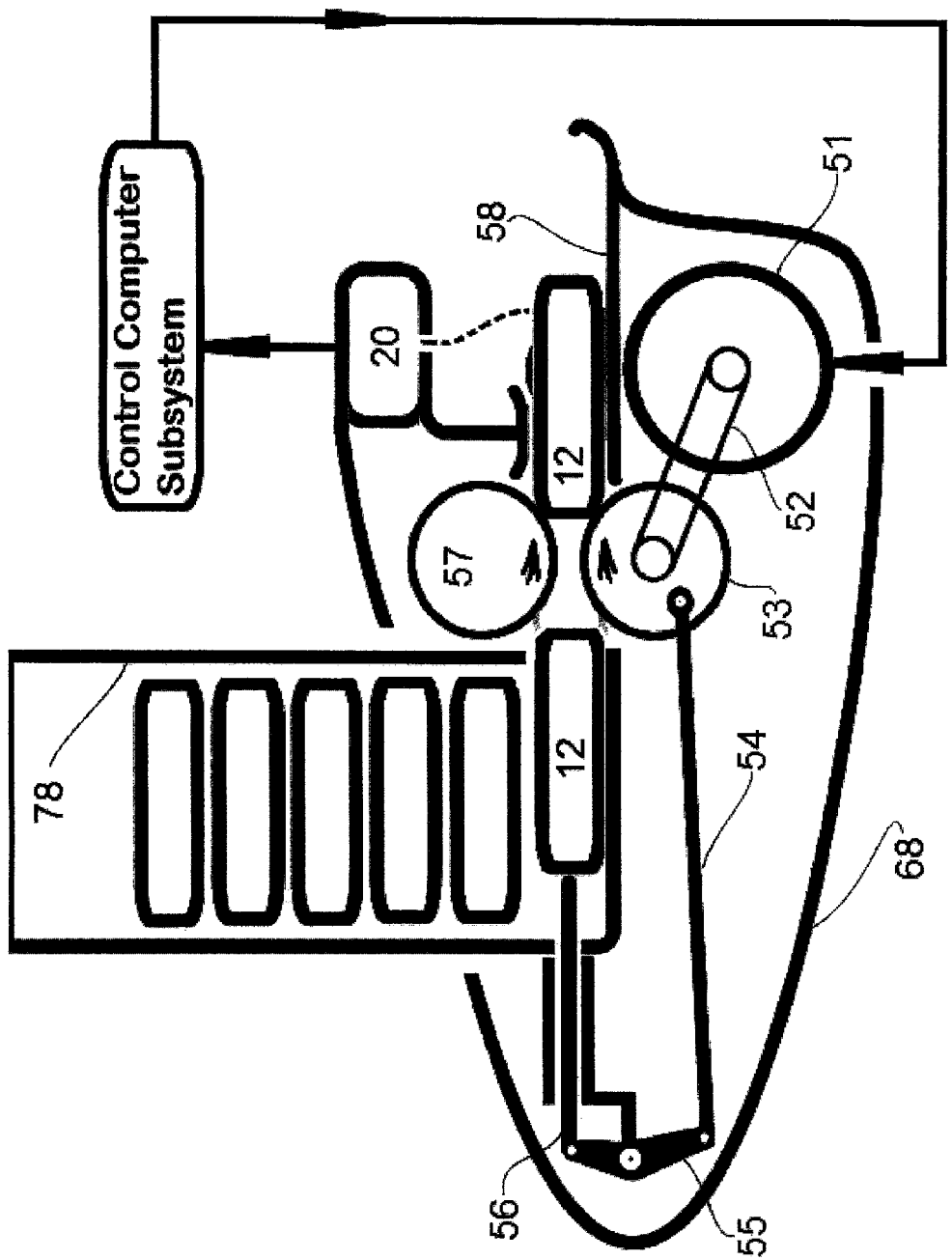
FIG. 7 is a partial schematic view of at least one embodiment of a dispensing kiosk or SST and a control computer subsystem.

Referring now to FIG. 7:
1. The PC workstation (of the control computer subsystem) sends a signal to dispensing motor 51 causing it to rotate clockwise one revolution.
2. The dispensing motor 51 is linked via drive chain 52 to drive roller 53 causing it to rotate clockwise one revolution.
3. One end of the first push rod 54 is attached to the periphery of the drive roller 53 causing it to move in an eccentric motion. The other end of the first push rod 54 is attached to the first end of rocker arm 55 causing it to rock in a clockwise direction.
4. The opposing end of rocker arm 55 is attached to the first end of the second push rod 56 causing its second end to push the next RTLS tag 12 out of the bottom of storage magazine 78 and into the drive roller 53.
5. The reusable RTLS tag 12 is trapped between the drive roller 53 and the idler roller 57 causing it to be ejected into dispenser tray 58.
6. As the reusable RTLS tag 12 is ejected into the dispenser tray 58 the idler roller 57 depresses push button switch 5 causing the RTLS tag 12 to send its unique IR signal 14 to IR receiver 20.
7. The PC workstation receives the unique ID of newly dispensed RTLS tag 12 from IR sensor 20 and associates patient's unique EMR identifier to the tag database 36 record for this tag ID 14.
8. The patient is instructed to retrieve and properly attach the newly dispensed RTLS tag 12 to their clothing.

The patient is now registered and their RTLS tag 12 is now recognizable by any SST 49 in the facility. When it recognizes the RTLS tag 12 of a registered patient, the SST 49 queries the tag database 36 from the EMR identifier associated to this tag 12 and retrieves all information regarding this patient and their current healthcare process from the CS 39. The SST 49 will now request only one of the alternate forms of ID accepted in the admit process as validation that the RTLS tag 12 is associated to the correct patient. If an accepted form of ID is presented and validated, the SST 49 then displays the following information through the user interface:
1. Validation that they are in the correct location or offer direction to the correct location for the next phase of their healthcare delivery process.
2. Progress along the current healthcare process (steps completed and steps yet to be completed).
3. Informational resources for any phase of their healthcare delivery process.

If the SST 49 discovers that the healthcare delivery process has been completed and patient discharge is required, the SST 49 will initiate the discharge if suitably equipped or direct the patient to a nearby SST 49 that is suitably equipped. The SST 49 will complete the discharge process as follows through the user interface:
1. Display a list of links to additional information and/or education regarding their diagnosis and treatment.
2. Display a patient satisfaction/patient suggestion survey for the patient to complete.
3. Print out a discharge information packet including discharge instructions, additional information requested and their survey responses.
4. The patient is asked to verify that they have read and understand the discharge instructions.
5. When the patient indicates they have read and understand the discharge instructions, the patient is asked to remove their RTLS tag 12 and place it into the RTLS tag return receptacle 70.

Figure 8:
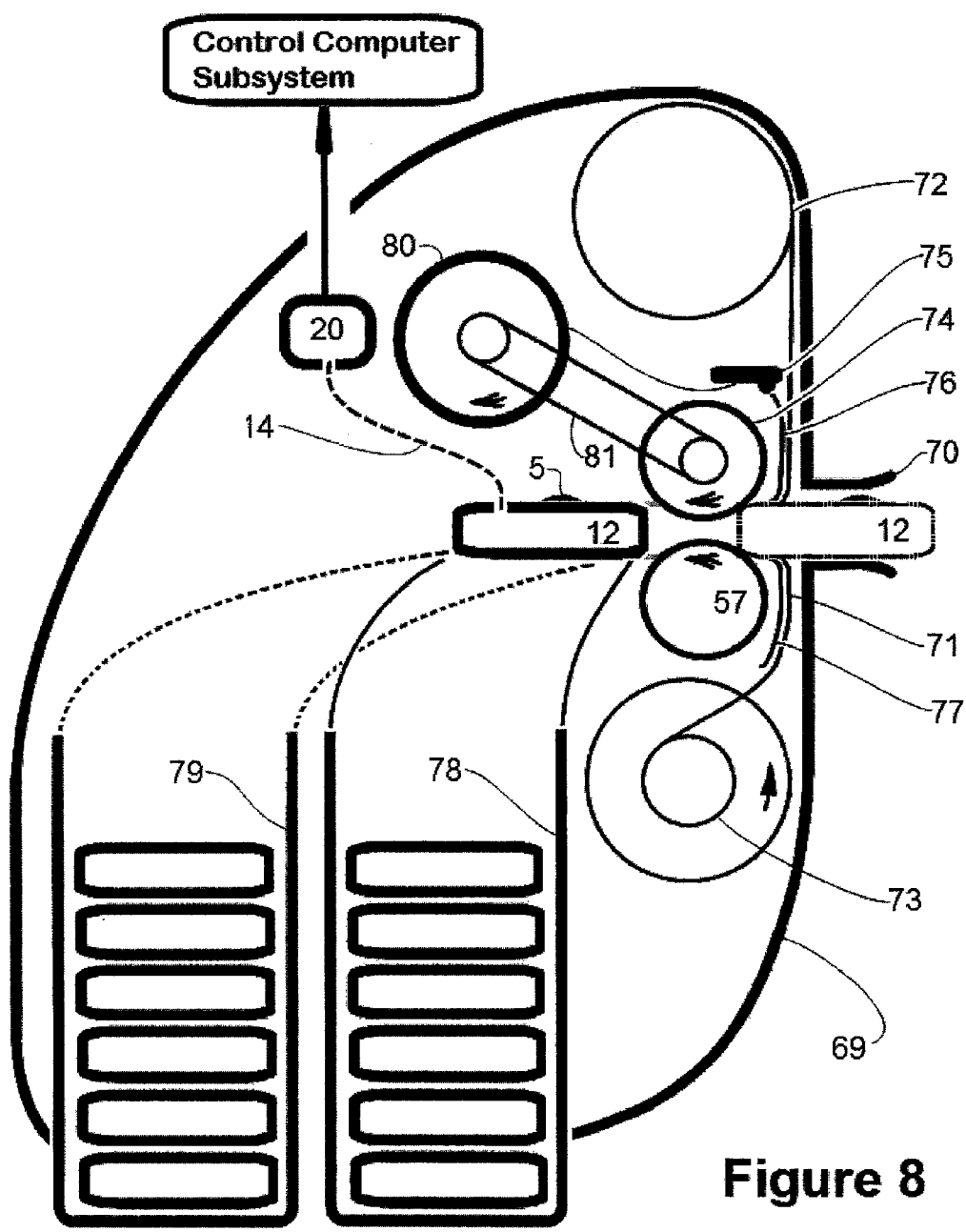
FIG. 8 is a partial schematic view of at least one embodiment of a receiving kiosk or SST and the control computer subsystem.

Turning now to FIG. 8 of the RTLS tag collector 69:
1. As the tag is inserted into the tag return receptacle 70, it passes through a perforated area of a moistened, flexible disinfectant wipe 71.
2. Two flexible shoes 76 and 77 are provided and allowed to float up and down to hold the flexible wipe 71 against the RTLS tag's 12 cross-sectional shape.
3. As the tag is inserted into the tag return receptacle 70 it causes the flexible shoe 76 to move upward activating the micro switch 75.
4. The micro switch 75 energizes the friction roller 74 drawing the RTLS tag into the RTLS tag collector 69.
5. As the RTLS tag 12 is drawn through with pressure on the top face of the tag 12, it depresses the tag alert button 5 and the RTLS tag's 12 IR signal 14 is analyzed.
6. If IR signal 14 proves to be satisfactory, the RTLS tag 12 is allowed to drop onto a reuse storage magazine 78 which, when full, will be taken to an admission SST 49.
7. If the tag's signals prove unsatisfactory, it is not suitable for return to service. The tag 12 is directed into a service magazine 79 which, when full, will be taken to the service area.
8. The wipe collection roller 73 advances drawing fresh flexible wipe 71 material from wipe feed roller 72, positioning its perforated slot to accept the next tag to be collected.
9. A wipe supply detection switch 82 remains depressed so long as the disinfectant wipe supply is sufficient. When supply is sufficiently depleted, the switch 82 is released, alerting staff that the disinfectant wipe supply must be replenished in SST 49.
10. The IR receiver 20 records the entry of the tag 12 into the SST 49, dissociates the patient's unique EMR identifier in the tag database 36 record for this tag ID 14 and sends the CDS 39 notification that discharge has occurred.
11. The SST 49 provides exit directions to the patient via the user interface.

A method described above defines rules in terms of conditional results derived from event data and subject data values, continually evaluates the rules in respect to the most recent event and subject data values, measures the performance of each clinical process corresponding to each rule, and acts to correct, in real time, the performance of any clinical process performance that is below that indicated in the rules design as provided.

The method includes providing a real-time locating tag which emits infrared (IR) and/or radio frequency (RF) signals representative of each tag's unique ID number to mobile subjects. The emitted signals are received by ceiling-mounted sensors with known locations in order to locate each subject that is involved in the clinical process. Each subject's identification data is associated with each unique tag ID number. The provision of this tag in a tracking environment allows the RTLS to associate unique tag data with a particular location and the time the tag was seen at that location.

The method optionally includes the provisions to notify the RTLS that other, non-location change events have occurred including but not limited to:
1. Classifying specific tag IDs into one or more tag type groups such as a "doctor" type, "nurse" type or "patient" type;
2. Implementing one or more "alert" switch(es) to the tag that may be manually or automatically activated to provide the RTLS notification of an event associated to the tag that is non-location based; and
3. Collecting and/or issuing external data event messages pertinent to specific tag IDs or tag types represented in a rule, such as network messages indicating new patient orders, the results of pending patient orders, and patient admission or discharge.

A system described above includes the aforementioned real-time locating tag in a RTLS environment; a means of storing and/or retrieving the current and historic values of all location and other pertinent CDS data events associated with each subject's unique ID tag; a processor means for continual evaluation of each rule in respect to the current data values stored for each event associated with each tag represented in each rule; and performance of the actions that may be associated with the specific values that may result from the evaluation of each rule.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A context-aware system for facilitating the delivery of healthcare to patients within a clinical environment monitored by real-time locating apparatus including auto-ID patient tags wherein patients having tags are located within the environment in real time by the apparatus, the system comprising:
    (a) a plurality of kiosks wherein at least one of the kiosks is a dispensing kiosk configured to store a plurality of reusable, auto-ID patient tags, including previously dispensed reusable tags, each of the stored, reusable tags being capable of transmitting signals used by the apparatus to establish real-time location of patients having the tags, each of the tags being capable of transmitting a wireless identification signal including ID information upon actuation and wherein the dispensing kiosk includes a dispensing mechanism to dispense stored tags and to actuate tags during dispensing of the tags by depressing a push button switch disposed on the tag so that each of the dispensed tags transmits the wireless identification signal upon depression of the push button switch; and
    (b) a control computer subsystem including a workstation coupled to the dispensing mechanism and including at least one user interface, the workstation being configured to send a first signal to the dispensing mechanism to dispense a stored tag and to actuate the stored tag during dispensing of the stored tag via the push button switch so that the dispensed tag transmits the wireless identification signal wherein the dispensing kiosk includes a first receiver coupled to the workstation to receive the wireless identification signal including its associated ID information and provide the ID information to the workstation.

2. The system as claimed in claim 1, wherein each dispensed tag is sanitized.

3. The system as claimed in claim 1, wherein at least one of the kiosks is a receiving kiosk including a receiving mechanism to receive previously dispensed tags.

4. The system as claimed in claim 3, further comprising means for sanitizing the received tags.

5. The system as claimed in claim 1, wherein at least one user interface includes at least one of a video camera, a display, a key pad or board, and a microphone, a touch screen, and a printer.

6. The system as claimed in claim 1, wherein at least one of the kiosks is a receiving kiosk including a second receiver coupled to the subsystem and a receiving mechanism to receive previously dispensed tags and to actuate tags during receiving of the tags wherein the second receiver receives the wireless signal from the actuated tag during receiving of the tag and provides the ID information to the subsystem.

7. A system comprising:
    (a) a tag comprising:
        (i) a push button switch, wherein the push button switch is movable between an undepressed position and a depressed position, wherein the tag has a thickness when the push button switch is in the depressed position;
        (ii) an infrared signal generator, wherein the infrared signal generator is operably coupled with the push button switch, wherein the infrared signal generator is configured to generate an infrared signal when the push button switch is in the depressed position; and
    (b) a kiosk comprising:
        (i) a keyboard;
        (ii) a display screen;
        (iii) a storage magazine, wherein the storage magazine defines an ejection slot, wherein the storage magazine is sized to receive the tag therein, wherein the ejection slot is sized to allow the tag to move therethrough;
        (iv) a push rod, wherein the push rod is movable between a first position and a second position to push the tag out of the ejection slot;
        (v) a first drive roller disposed proximate the ejection slot, wherein the first drive roller is operably connected to the push rod;
        (vi) a dispensing motor, wherein the dispensing motor is operably connected to the first drive roller, wherein the dispensing motor is configured to rotate the first drive roller and simultaneously move the push rod from the first position to the second position;
        (vii) a second drive roller disposed proximate the ejection slot, wherein the second drive roller is spaced a distance apart from the first drive roller, wherein the distance is equal to the thickness of the tag when the push button switch is in the depressed position, wherein the first drive roller and the second drive roller are configured to receive the tag as the tag passes out of the ejection slot and move the push button switch into the depressed position as the tag passes therethrough; and
        (viii) an infrared signal receiver, wherein the infrared signal receiver is oriented to receive the infrared signal generated by the tag.

8. The system of claim 7, the kiosk further comprising a rocker arm having a first end and a second end, wherein the first end of the rocker arm is connected to the push rod, wherein the second end of the rocker arm is operably connected to the first drive roller.

9. The system of claim 8, the kiosk further comprising a drive rod having a first end and a second end, wherein the first end of the drive rod is connected to the second end of the rocker arm, wherein the second end of the drive rod is connected to the first drive roller.

10. The system of claim 9, the kiosk further comprising a drive chain, wherein the drive chain is connected to the first drive roller and the dispensing motor, wherein the dispensing motor rotates the first drive roller via the drive chain.

11. The system of claim 7, the kiosk further comprising a return receptacle, wherein the return receptacle is sized to receive the tag therein.

12. The system of claim 11, the kiosk further comprising a third drive roller disposed proximate the return receptacle.

13. The system of claim 12, the kiosk further comprising:
(a) a micro switch operably coupled with the third drive roller; wherein the micro switch is movable between an undepressed position and a depressed position, wherein the micro switch actuates the third drive roller in the depressed position; and
(b) a flexible shoe, wherein the flexible shoe is movable between a first position and a second position, wherein the flexible shoe is configured to depress the micro switch when the flexible shoe is in the second position.

14. The system of claim 13, the kiosk further comprising:
(a) a wipe feed roller; and
(b) a flexible wipe, wherein the flexible wipe extends between the wipe feed roller and the flexible shoe.

15. The system of claim 13, the kiosk further comprising a storage magazine, wherein the storage magazine is adjacent to the service magazine.

16. A method comprising:
(a) authenticating a user of a kiosk, wherein the kiosk includes a housing;
(b) in response to authenticating the user of the kiosk, retrieving a record associated with the user; and
(c) ejecting a tag from a storage magazine disposed inside the housing into a storage tray accessible by the user, the ejecting comprising:
(i) pressing the tag into a pair of rollers;
(ii) rolling the tag through the pair of rollers;
(iii) depressing a push button switch disposed on the tag as the tag rolls through the pair of rollers;
(iv) in response to depressing the push button switch, generating an identification signal from a signal generator of the tag, wherein the identification signal is associated with the tag;
(v) sensing the identification signal with a signal receiver disposed in the housing; and
(vi) in response to sensing the identification signal; associating the record with the tag.

17. The method of claim 16, further comprising:
(a) receiving the tag into a tag return receptacle;
(b) in response to receiving the tag into the tag return receptacle, actuating a second pair of rollers; and
(c) in response to actuating the second pair of rollers, pulling the tag through the second pair of rollers into the housing.

18. The method of claim 17, further comprising:
(a) in response to receiving the tag into the tag return receptacle, moving a flexible shoe from a first position to a second position;
(b) in response to moving the flexible shoe to the second position, actuating a micro switch; and
(c) in response to actuating the micro switch, actuating the second pair of rollers.

19. The method of claim 18, further comprising:
(a) determining whether the tag should be disposed in a service magazine or the storage magazine;
(b) in response to determining the tag should be disposed in the service magazine, disposing the tag in the service magazine; and
(c) in response to determining the tag should be disposed in the storage magazine, disposing the tag in the storage magazine.

20. The method of claim 19, further comprising:
(a) depressing the push button switch disposed on the tag as the tag rolls through the second pair of rollers;
(b) in response to depressing the push button switch, generating the identification signal;
(c) sensing the identification signal with a second signal receiver disposed in the housing; and
(d) determining whether the tag should be disposed in a service magazine or the storage magazine based at least in part on the identification signal.

\* \* \* \* \*